United States Patent [19]

Acharya

[11] Patent Number: 5,741,805
[45] Date of Patent: Apr. 21, 1998

[54] CONTROLLED RELEASE PILOCARPINE DELIVERY SYSTEM

[75] Inventor: Ramesh N. Acharya, Lake Forest, Ill.

[73] Assignee: OraMed, Inc., Lake Forest, Ill.

[21] Appl. No.: 435,285

[22] Filed: May 5, 1995

Related U.S. Application Data

[63] Continuation of Ser. No. 907,852, Jul. 2, 1992, abandoned.
[51] Int. Cl.⁶ ................................................. A61K 31/415
[52] U.S. Cl. ........................................ 514/397; 514/772
[58] Field of Search ................................. 514/397, 772

[56] References Cited

U.S. PATENT DOCUMENTS

| | | |
|---|---|---|
| 3,640,741 | 2/1972 | Etes . |
| 4,151,270 | 4/1979 | Ream et al. . |
| 4,209,505 | 6/1980 | Mikhail . |
| 4,438,100 | 3/1984 | Balslev et al. . |
| 4,615,697 | 10/1986 | Robinson . |
| 4,820,506 | 4/1989 | Kleinberg et al. . |
| 4,900,552 | 2/1990 | Sanvordeker et al. . |
| 4,906,455 | 3/1990 | Hoerman . |
| 4,917,674 | 4/1990 | Molinoff . |
| 4,938,963 | 7/1990 | Parnell . |
| 4,988,679 | 1/1991 | Chavkin et al. . |

FOREIGN PATENT DOCUMENTS

| | | |
|---|---|---|
| WO 91/01130 | 2/1991 | WIPO . |
| WO 92/00044 | 1/1992 | WIPO . |
| WO 92/03124 | 3/1992 | WIPO . |

OTHER PUBLICATIONS

Fox et al., "Xerostomia: evaluation of a symptom with increasing significance" *J. Am. Dent. Assoc.* (1985) 110:519–525.
Chencharick et al., "Nutritional consequences of the radiotherapy of head and neck cancer" *Cancer* (1983) 51:811–815.
Fox, "Management of salivary gland hypofunction and dry mouth (xerostomia)" *Head and Neck Cancer*, Fee et al., eds., (1990) pp. 322–324.
Fox, "Systemic therapy of salivary gland hypofunction" *J. Dent. Res.* (1987)66:689–692.
LeVeque et al., "A multicenter, randomized, double–blind, placebo–controlled, dose–titration study of oral pilocarpine for treatment of radiation–induced xerostomia in head and neck cancer patients" *J. Clin. Oncol.* (1993) 11:1124–1131.
Johnson et al., "Oral pilocarpine for post–irradiation xerostomia in patients with head and neck cancer" *N. Engl. J. Med.* (1993) 329:390–395.
Greenspan et al., "Effectiveness of pilocarpine in postradiation xerostomia" *Cancer* (1987) 59:1123–1125.
Dawes, "The composition of human saliva secreted in response to a gustatory stimulus and to pilocarpine" *J. Physiol.* (London) (1966) 183:360–368.
Mandel et al., "The effect of pharmacologic agents on salivary secretion and composition. II. Isoproterenol, alpha and beta adrenergic blockers" *J. Oral. Ther. Pharmacol.* (1968) 4:260–269.

Fox et al., "Pilocarpine for the treatment of xerostomia associated with salivary gland dysfunction" *Oral Surg. Oral Med. Oral Pathol.* (1986) 61:243–248.
Rhodus et al., "Effects of pilocarpine on salivary flow in patients with Sjögren's syndrome" *Oral Surg. Oral Med. Oral Pathol.* (1991) 72: 545–549.
Greco et al., "Systemic pilocarpine toxicity in the treatment of angle closure glaucoma" *Ann. Opthalmol.* (1973) 5:57–59.
Kastl, "Inadvertent systemic injection of pilocarpine. Case report" *Arch. Opthalmol.* (1987) 105:28–29.
Littmann et al., "Severe symptomatic atrioventricular block induced by pilocarpine eye drops" *Arch. Intern. Med.* (1987) 147:586–587.
Weaver et al., "Pilocarpine disposition and salivary flow responses following intravenous administration to dogs" *Pharm. Res.* (1992) 9:1064–1069.
Valdez et al., "Interactions of the salivary and gastrointestinal systems. II. Effects of salivary gland dysfunction on the gastrointestinal tract" *Dig. Dis.* (1991) 9:210–218.
Hughes et al., "Oral–pharyngeal dysphagia: A common sequela of salivary gland dysfunction" *Dysphagia* (1987) 1:173–177.
Caruso et al., "Objective measures of swallowing in patients with primary Sjögren's syndrome" *Dysphagia* (1989) 4:101–105.
Helm, "Role of saliva in esophageal function and disase" *Dysphagia* (1989) 4:76–84.
Korsten et al., "Chronic xerostomia increases esophageal acid exposure and is associated with esophageal injury" *Am. J. Med.* (1991) 90:701–706.
Schuller et al., "Treatment of radiation side effects with oral pilocarpine" *J. Surg. Oncol.* (1989) 42:272–276.
Severin, "Keratoconjunctivitis sicca" *Vet. Clin. North Am.* (1973) 3:407–422.
Pavan–Langston, "Potential use of ocular–insert therapy in dry eyes" *Int. Opthalmol. Clin.* (1973) 13:231–238.
Deshpande et al., "Sustained release ophthalmic formulations of pilocarpine" *J. Pharm. Pharmacol.* (1988) 41:197–200.
Lehr et al., "A surface energy analysis of mucoadhesion: Contact angle measurements on polycarbophil and pig intestinal mucosa in physiologically relevant fluids" *Pharm. Res.* (1992) 9:70–75.
Physician's Desk Reference for Ophthalmology, Walsh, J.B. et al., eds., 16th Edition (1988) pp. 3, 11.
Abstract of Mamtani et al., "Comparison of total costs of administering calcium polycarbophil and psyllium mucilloid in an institutional setting" *Clin. Therap.* (1990) 12:22–25.
Embase Abstract of Arch. Intern. Med. (USA), 1991, 151/6 (1149–1152). Fox et al.

*Primary Examiner*—Zohreh Fay
*Attorney, Agent, or Firm*—Leydig, Voit & Mayer, Ltd.

[57] ABSTRACT

There is disclosed a method for treating a patient suffering from xerostomia, xerophthalmia or excessive intraocular pressure. The method comprises administering to said patient a therapeutically effective amount of pilocarpine, or a pharmaceutically acceptable salt thereof, in an amount sufficient to maintain a blood serum level of pilocarpine in said patient of from about 5 to about 40 ng/ml, for a period of at least 6 hours. Controlled release unit dosage forms containing pilocarpine are also disclosed.

8 Claims, 5 Drawing Sheets

CONTROLLED RELEASE PILOCARPINE DELIVERY SYSTEM

This application is a continuation of application Ser. No. 07/907,852, filed Jul. 2, 1992. Now abandoned.

FIELD OF THE INVENTION

This invention relates generally to xerostomia, commonly known as "dry mouth syndrome", and to xerophthalmia, a dryness of the conjunctiva and cornea. More particularly, the present invention relates to method for alleviating the symptoms of xerostomia or xerophthalmia in an affected patient. Additionally, this invention relates to a method for alleviating excessive intraocular pressure.

BACKGROUND OF THE INVENTION

Normally an individual produces 0.5 to 1 liter per day of saliva. Although varying greatly between individuals, on average 65 percent of saliva is submandibular, 23 percent from the parotids, 8 percent from the minor mucous, and 4 percent sublingual.

Xerostomia is a condition in which the salivary glands do not produce sufficient quantities of saliva. This causes discomfort which can in some cases be quite severe. Without saliva, the mouth burns and the throat and tongue can undergo radical changes. Teeth can decay rapidly and the tongue can become smooth, cracked and vulnerable to infection. There is often a loss of taste and, because saliva contains important digestive enzymes, there are often problems with digestion.

The persistence of a dry mouth at night can disturb sleep causing the individual suffering from it to waken frequently, even every hour. Furthermore periodontal disease and increased tooth decay as well as loss of teeth can be a result of xerostomia.

The mouth is one of the body areas most exposed to the external environment. Normally, mucous forms a continuous protective layer in the nose, mouth and throat. A patient suffering from xerostomia not only has decreased fluid in the mouth, but also an insufficient quantity of mucoproteins and mucopolysaccharides to hold fluid in contact with the cells and create a barrier to irritation and infection.

The onset of the effects of xerostomia is insidious with no clear line of demarcation when one has or has not the malady. Also different individuals may have different symptoms to a differing extent in a different succession. Dry mouth is the most common symptom. Alteration of taste sensation leads to change in the selection and perception of food. After alteration comes taste desensitation, which may lead to lack of any taste.

Sores on any of the mucous tissues of the oral area (tongue, gums, mouth, cheeks etc.), ulcerations, fissures, swellings, bleeding, coatings, even erosion of the tongue are all possible. With the decrease in saliva comes incomplete digestion, buildup of food, plaque, gingival hemorrhage, soreness at dental bridges, and extreme breath malodor. Also possible are swelling of various mouth tissues and possibly difficulty of speech. The lips may become desiccated or cracked. The rate of dental caries may increase dramatically.

It is estimated that several million individuals suffer from this condition nationwide. The actual number of individuals suffering from xerostomia is not known, however, because until recently there has been little acknowledgement of the prevalence or severity of the problem. It is estimated that about ten percent of the population over 50 years of age and 25 percent of the population over 65 years of age suffer from xerostomia. The majority of those affected are women.

Some direct primary causes of xerostomia are autoimmune diseases such as Sjogren's syndrome, medical irradiation, malnutrition, hormonal imbalance, arthritis and aging. When areas of the head or neck are medically irradiated by as little as 1000 rads per week, 85 percent of the patients suffer from xerostomia after six weeks and 95 percent after three months.

Radiation xerostomia onsets rapidly with a greater than 50 percent decrease in salivary flow after one week and a greater than 75 percent decline after six weeks of treatment. The xerostomia is progressive, persistent, and irreversible, reaching a greater than 95% reduction in saliva output three years after radiation. In patients where only part of the major salivary glands are in the path of the ionizing radiation, the non-exposed portion may undergo hyperplasia and partly compensate for the damaged acini. The most severe cases of xerostomia are caused by radiation therapy after head and neck surgery and by autoimmune diseases such as lupus, Sjogrens Syndrome, and rheumatoid arthritis. See, for example, P. C. Fox et al., J. Am. Dental Assoc. 110:519–525 (1985).

Decreased salivation during the post radiation therapy may have a significant impact on the patients' quality of life, already impaired by the "bad news" of having cancer and numerous complications of chemo and radiotherapy such as nausea cephalalgia and dysphagia. As indicated above, saliva is important for the preservation of oral hard and soft tissues and for the normal execution of oral functions such as taste, swallowing and speech.

Secondarily, xerostomia is a side effect from the administration of over 400 drugs, including major antihypertensives, antidepressants, antispasmodics, diuretics, muscle relaxants, antipsychotics, appetite depressants, and therapeutics for Parkinson's disease.

In addition to radiation and chemotherapy induced salivary dysfunctions, a variety of other chronic inflammation and other immune disorders are also known which are characterized by diminished lacrimal and salivary gland secretions, e.g., Sjogren's syndrome. This is a chronic condition resulting in kerato-conjunctivitis sicca (KCS) and xerostomia.

The treatment of Sjogren's syndrome is aimed at symptomatic relief and limiting the damaging local effects of chronic xerostomia and xerophthalmia, which is a dryness of the conjunctiva and cornea. Ocular dryness responds to the use of artificial tears which may have to be applied as frequently as every 30 minutes. Slow release tear formulations are reported in the literature with limited success. Soft contact lenses are recommended to protect the cornea but increase the risk of infection. Saran wrap occlusion or diving goggles at night have been proposed to prevent tear evaporation. Xerostomia in Sjogren's patents is difficult to treat, but may temporarily relieved by frequent intake of water or artificial salivas, chewing gums, candies, etc.

Cases of xerostomia may vary from the mild, in which only slight dryness is experienced, to severe cases in which the patient will have serious problems with mastication, swallowing, digestion, speech, and the like. Breathing through the mouth may also induce xerostomia. Further, seasonal induced xerostomia is also experienced by some individuals. As noted in U.S. Pat. No. 4,438,100 to Balslev et al., other causes of xerostomia include the physiological (e.g., age, menopause, postoperative conditions, dehydration), as well as the psychic (nervousness).

Until recently, the treatments for xerostomia have had significant drawbacks. For example, symptoms of mild xerostomia can be somewhat alleviated by consumption of fluids, hard candy and throat lozenges. Food, in general, increases salivary flow. It has been known that the effects of secondary xerostomia may be broadly alleviated by sweet, sour, or bitter foods such as sweet candies, lemon drops, peppermint drops, chewing gum, and the like. Because of the susceptibility of xerostomia patients to tooth decay and gum disease, however, the increased sugar intake associated with conventional candy and lozenges is of real concern. In addition, fluids or candy are typically not effective with more severe cases of xerostomia, nor do they provide long-lasting relief with mild cases.

One general approach to xerostomia is the use of synthetic saliva. There are a number of artificial salivas on the market which contain alcohol, mineral oils, glycerine, and combinations of polyethylene glycols. There are many commercial brands, based on either pig mucin or carboxymethylcellulose (CMC), and including all the requisite electrolytes, buffer, and optional flavorants and/or sweeteners. The usual electrolytes are potassium, sodium, magnesium, calcium, chloride, bicarbonate, phosphate, and fluoride. Except for one Danish brand (Saliva-Orthana) and one Dutch experimental type based on mucin, most artificial salivas are based on CMC, such as those sold under the marks Orex® (Young Dental), Xero-Lube® (Scherer), Moi-Stir® (Kingswood Laboratories), and Salivart® (Westport Pharmaceuticals). Va-Oralube (First Texas Labs., Dallas) contains sorbitol and fluoride in addition to the appropriate electrolytes and CMC. Moi-Stir (Kingswood Co., Toronto) has a high sodium content and is mint flavored. Salube (Oraphorm Co., Australia) comes in small dropper bottles. Saliment (Richmond Pharm. Co., Ontario), also based on CMC, is lemon flavored. Xero-lube (Scherer Labs., Dallas, Tex.), Artisial (jouvenal, Paris, france), and Glandosane (Fresenius, Bad Homburg, West Germany) are available in ordinary spray bottles. Glycerine, hydroxyethylcellulose, and polyethylene oxides may also be found as bases for synthetic salivas. Many patients find, however, that such preparations are irritating or distasteful, and that their lubricating effect is of relatively short duration.

Another broad approach to alleviating the symptoms of xerostomia is to fit the mouth with a constant or controllable reservoir of synthetic saliva via a permanent or removable dental device. Palatal reservoirs require repeated refillings. A removable maxillary denture with reservoir rim is less cumbersome. It has several holes for filling with a syringe, drainage in use, and then washing after every meal. The removable denture with rim has space for about 3 ml of synthetic saliva. This denture, is expensive since custom-made, has an uncomfortable thickness, may hinder speech, and must be cleaned and refilled several times per day. J. A. Toljanic in Quintessence of Dental Technology, June 1985, pp. 355–358 and The Journal of Prosthetic Dentistry, volume 52, No. 4, pp. 540–544 shows pictures, gives directions, and has a bibliography on this subject. An informative background reference on xerostomia is P. C. Fox et al. (1985), J. Am. Dental Assoc. 110:519–525 (1985). There has also been some experimentation with parasympathomimetic drugs, i.e., drugs that mimic the action of the parasympathetic nervous system which controls salivation. There have been reported dosage control problems with these drugs, however, as well as significant side effects. These are generally administered in the form of tablets or capsules. Drugs which are known to be direct sialogogues include:

(a) pilocarpine compounds such as the hydrochloride, nitrate, or jaborandi leaves or their extracts;

(b) neostigmine and its bromide, distigmine bromide (Ubretid), pyridostigmine bromide (Mestinon);

(c) nicotinic acid, nicotinamide (Nicobion 500), and benzopyrone (Venalot); and (d) carbachol (Doryl), potassium iodide, and anetholthrithion (Sulfarlem S 25)

Drugs known to be indirect sialogogues include:

ascorbic acid (Vitamin C), citric acid tablets, malic acid, lemon glycerine swabs, and paraffin wax.

The above information has been reviewed by Imfeld in volume 13, number 4, of Acta Parodontologics at pp. 1083/111-10996/124 (1984) and by Vissink et al. at volume 129, number 43 of Ned Tijdschrift Geneesked at pp. 2054–2057 (1985).

The following references relate to compositions and methods for treating xerostomia:

U.S. Pat. No. 4,438,100 to Balslev et al. discloses a viscous artificial saliva containing a mucine and an oxidizing bactericide.

U.S. Pat. No. 4,209,505 to Mikhail discloses a mouthwash for dry mouth relief, containing pilocarpine or a pilocarpine derivative. It is also noted therein notes that various types of diets have also been used (albeit unsuccessfully) in an attempt to alleviate xerostomia.

U.S. Pat. No. 4,151,270 to Ream et al. teaches a chewing gum composition formulated to stimulate salivation. The gum contains fructose and an organic acid such as adipic, ascorbic, citric, fumaric, lactic, malic or tartaric acids.

U.S. Pat. No. 4,938,963 discloses a method for treating xerostomia, comprising orally administering, to an affected individual, an amount of an eriodictyon fluid composition effective to alleviate the symptoms of dry mouth, the eriodictyon fluid composition comprising eriodictyon fluid extract and sweetener.

U.S. Pat. No. 4,917,674 discloses a medical device for the treatment of an individual suffering from xerostomia comprising two mouth moisturizing pads, each of which hold at least one sponge section wherein the sponge section is saturable with water for gradual dispensing of said water in the mouth.

U.S. Pat. No. 4,906,455 discloses a method for treating xerostomia wherein the patient chews, for a period of at least about 20 minutes, a gum containing a food-grade organic acid selected from the group consisting of adipic, fumaric, succinic, suberic, sebacic, azelic and pimelic acids.

U.S. Pat. No. 4,820,506 teaches a composition for promoting the production of human saliva consisting essentially of an aqueous liquid solution of water having dissolved therein:

(a) from about 2 to about 3 weight percent food-grade organic acidulent;

(b) a food-grade sweetener benign to stomic microflora selected from the group consisting of a sugar, a synthetic sweetener, and a reduced, sugar-related compound, and (c) a saturated calcium phosphate solution.

The treatment of xerostomia with orally ingested pilocarpine is known in the art. Pilocarpine as 5 mg. capsules or tablets three to four times a day has been reported to show marked improvement in the salivary function along with manifestation of numerous side effects. Such treatment, however, presents a problem as pilocarpine is a highly potent parasympathomimetic drug which acts upon numerous parasympathomimetic responsive sites in the body. Because of this, the drug has many potential side effects and its therapeutic blood level concentration and toxic blood level concentration are not too far apart.

It is also known that pilocarpine can be used to treat xerophthalmia, a dryness of the conjunctiva and cornea. Further, pilocarpine has been used to alleviate excessive intraocular pressure. Unfortunately, the treatment of xerophthalmia and excessive intraocular pressure, by administration of pilocarpine to a patient in need of such treatment, is accompanied by the same problems as with respect to the treatment of xerostomia with orally ingested pilocarpine. Thus, a need has arisen for a method for treating xerophthalmia and excessive intraocular pressure, by administration of pilocarpine to a patient by a means that is efficacious, yet substantially free of the normally associated side-effects of pilocarpine therapy, such as sweating, flushing, stomach cramps.

SUMMARY OF THE INVENTION

The present invention provides a method for treating a patient suffering from xerostomia, xerophthalmia, or excessive intraocular pressure, comprising administering to said patient a therapeutically effective amount of pilocarpine, or a pharmaceutically acceptable salt thereof, in an amount sufficient to maintain a blood serum level of pilocarpine in said patient of from about 5 to about 40 ng/ml, for a period of at least 6 hours. It has been discovered that by maintaining the pilocarpine at such a serum level, the therapeutically beneficial results of the pilocarpine can be achieve, such as the effective alleviation of the symptoms of xerostomia, xerophthalmia, and excessive intraocular pressure.

The present invention also provides a method for preventing xerostomia in a patient who is to receive radiotherapy comprising administering to said patient a prophylactically effective amount of pilocarpine, or a pharmaceutically acceptable salt thereof, prior to the commencement of radiotherapy, in an amount sufficient to maintain a blood serum level of pilocarpine in said patient of from about 5 to about 40 ng/ml, for a period of at least 6 hours.

Additionally, the present invention provides a method for preventing xerostomia in a patient who is to receive chemotherapy comprising administering to said patient a prophylactically effective amount of pilocarpine, or a pharmaceutically acceptable salt thereof, prior to the commencement of chemotherapy in an amount sufficient to maintain a blood serum level of pilocarpine in said patient of from about 5 to about 40 ng/ml, for a period of at least 6 hours.

Further, the present invention provides a controlled release formulation of pilocarpine that is capable of releasing pilocarpine at such a rate that a blood serum level of about 5 to about 40 ng/ml can be achieved for an extended period of time, such as about six hours, or more. The formulation is a unit dosage form comprising an intimate admixture of pilocarpine and calcium polycarbophil, wherein from about 5 to about 30 mg of pilocarpine is present and the ratio of calcium polycarbophil to pilocarpine is from about 10:1 to about 20:1.

DETAILED DESCRIPTION OF THE PREFERRED EMBODIMENTS

The present invention provides several advantages over the prior art tablets of pilocarpine. As pilocarpine is a highly potent parasympathomimetic drug which acts upon numerous parasympathomimetic responsive sites in the body, the drug has many potential side effects and its therapeutic blood level concentration and toxic blood level concentration are not too far apart. The controlled release delivery described herein allows a better control and tighter control over the serum levels achieved and therefore offers a much better therapeutic approach for the management of xerostomia and xerophthalmia.

Additionally, pilocarpine, as a standard oral tablet, capsule, or liquid, because of its potent nature and partly due to its short biological half life is usually administered in several doses of 5 mg. each over 24 hours. This requires frequent dosing. Most xerostomiacs are elderly patients with other severe stressful physiological conditions. An exact and orderly self medication is extremely difficult to achieve with such conventional oral delivery systems.

Preferably, from about 0.1 to about 30 percent, by weight, of carbomer polymer and, from about 0.1 to about 30 percent, by weight, of hydroxy methyl cellulose and/or hydroxy propyl methyl cellulose is present in the unit dosage.

The prolonged or extended delivery approach of the present invention requires only one or two doses per 24 hours or less, and offers better delivery, for more accurate and reproducible dosing in the proposed patient population either at home or in institutionalized environments.

Most importantly, the prior art orally administered conventional dosage forms produce a very high initial blood concentration. The decay of the blood level is dependent upon many biological factors and usually the drug concentration in the blood falls below its therapeutically effective level before the next dose is delivered. Thus, the prior art orally administered drugs have initially high blood concentrations which causes undesirable side effects and subsequently subtherapeutic levels during which the patient does not experience the desirable therapeutic effects and is unprotected. The prolonged or extended dose forms of the present invention, because of their uniform delivery rates, minimize the "hill and valley" effects and provide a better therapeutic control of xerostomia and xerophthalmia, or control of intraocular pressure.

The principal aspect of the present invention is the discovery that by maintaining a serum level of pilocarpine from about 5 to about 40 ng/ml, the desired therapeutic efficacy can be achieved, without the undesired side effects, as discussed above. Preferably, the serum level will be maintained from about 5 to about 25 mg/ml. Such a level is sufficient to stimulate saliva flow, to provide fluid flow to the conjunctiva and cornea, and to alleviate intraocular pressure. At the same time, such a serum level does not cause any adverse cardiovascular effects and does not cause sweating, flushing, or stomach cramps.

The exact method by which the desired serum level is achieved is not critical. Preferably, a controlled oral delivery system is employed, although other delivery means could be employed, so long as they have been modified to achieve the desired serum level for an extended period of time, such as from about 6 to about 24 hours, or more, preferably for at least about 8 hours, more preferably for at least about 10 hours, and most preferably for at least about 12 hours. Suitable specific forms of administration include the forms for the oral route such as tablets, capsules, powders, granules and oral solutions or suspensions, buccal and sublingual forms of administration, subcutaneous, intramuscular or intravenous forms of administration and rectal forms of administration. For topical application, the compounds according to the invention may be used in creams, ointments or lotions.

The blood serum pilocarpine levels referenced in this application and the appended claims, unless otherwise denoted, are meant to refer to average levels determined across a representative patient base. Obviously, because individual differences, such as with respect to blood chemistry (enzyme content and level), liver function, and the like, the half-life of pilocarpine may vary drastically from individual to individual.

Thus, it is possible that for some individuals taking the dosage forms of the present invention, those individuals will not experience the target serum level for the full desired time. However, such individuals will still obtain the benefits of the present invention, as the target level will still be maintained for a significantly longer period of time than could be achieved by those individuals taking conventional immediate release forms of pilocarpine.

Further, for some unique individuals, it is possible that the conventional immediate release forms of pilocarpine may result in a serum profile that is reflective of an extended release period. For those individuals, the present dosage forms will provide even longer periods wherein the individual exhibits the target serum level of pilocarpine, reducing the number of times that individual will need to be administered subsequent dosage forms.

Pilocarpine analysis in plasma should be performed using the following general HPLC analytical method:

Blood samples are collected in a heparinized tube containing suitable levels of enzyme inactivator NaF. Plasma is separated by centrifuging the samples for about 5 to 10 minutes using a standard clinical centrifuge. Plasma is removed and an additional quantity of NaF is added to deactivate the enzymes. The plasma samples are kept frozen until they are ready for analysis.

Plasma samples are then allowed to come to room temperature. The samples are centrifuged again to remove excess sodium fluoride. Aliquot samples of plasma are removed and a known amount of an internal standard—pilosine is added. The samples are extracted with the aliquot quantity of methylene chloride. The organic phase is removed and the solvent is evaporated at 40° C. under a gentle stream of nitrogen, to dryness. A known quantity of 1 mM HCl is added and the sample is extracted with ether to remove other organic matters. The aqueous phase is dried under vacuum to remove any residual ether. The samples thus prepared are analyzed by HPLC using the following conditions.

Mobile Phase: 55/30/15 mixture of 7 mM Potassium phosphate pH 4.0/acetonitrile/methanol.

Column: 150 cm×4.6 mm I.D. containing 5 microns Spherisorb ODS-1.

Detector UV Detector at 214 nm. Flow rate 1.2 ml/minutes.

The above conditions may be optimized to obtain proper separation, if necessary. Concentrations of pilocarpine in plasma are determined by comparing peak height ratio (of pilocarpine/internal standard) between experimental samples and calibration standards.

The formulations may conveniently be presented in unit dosage form and may be prepared by any of the methods well known in the art In a preferred embodiment, the delivery system is a unit dosage form comprising an intimate admixture of pilocarpine and calcium polycarbophil, wherein from about 5 to about 30 mg of pilocarpine is present and the ratio of calcium polycarbophil to pilocarpine is from about 10:1 to about 20:1. The controlled release compositions of the present invention may be formed directly with calcium polycarbophil and pilocarpine, or a salt thereof, with or without other excipients, by granulation, direct procedures, such as direct compression, direct extrusion, direct blending and direct molding.

The sustained release matrix may optionally include additional edible non-toxic ingredients, such as are conventionally employed in medicinal dosage forms. Thus, the compositions of the invention may optionally include one or more excipients in an amount within the range of from about 0.1% to about 99% by weight and preferably from about 1% to about 95% by weight, such as lactose, mannitol, corn starch, potato starch, microcrystalline cellulose, carbomer polymers, hydroxy methyl cellulose, hydroxypropyl methyl cellulose, polyvinyl pyrrolidone, acacia, gelatin, croscarmellose sodium, talc, magnesium stearate, stearic acid, and other excipients, colorants, diluents, buffering agents, moistening agents, preservatives, flavoring agents, and pharmacologically compatible carriers. Other conventional ingredients which may optionally be present include preservatives, stabilizers, plasticizers, cosolvents, antiadherents or silica flow conditioners or glidants, such as Syloid brand silicon dioxide as well as FD&C colors.

EXAMPLE 1

PREPARATION OF DOSAGE FORMS

Quantitative Composition of the Drug

The following is a quantitative composition of a master granulation used to prepare three strengths of pilocarpine hydrochloride controlled release tablets—5 mg, 20 mg and 25 mg.

| Ingredients | % w/w | Per 20 Kg Batch |
| --- | --- | --- |
| Pilocarpine Hydrochloride, USP | 4.630[1] | 0.926 Kg |
| Carbomer 934P NF (Carbopol 934P) | 4.630[2] | 0.926 Kg |
| Hydropropyl Methylcellulose, USP (Methocel E4M Premium CR Grade[5] | 9.280[2] | 1.856 Kg |
| Calcium Polycarbophil, USP | 80.460[2] | 16.092 Kg |
| Magnesium Stearate, NF (to be added in dry granulation) | 1.000[2] | 0.2000 Kg |
| Alcohol, USP (20% V/V in Purified Water USP)[4] | QS[3] | QS |
| | 100.00% | 20.000 Kg |

[1]An overage up to 5% of label claim was used, if necessary, to compensate for manufacturing losses.
[2]Quantity of inactive agents was adjusted from 90 to 100% of the indicated values.
[3]Alcohol content of the granulation and drying equipment used. The granulation fluid was varied from 0 to 20% V/V depending upon the granulation fluid was removed during the drying of the granulation mass.
[4]Dehydrated Alcohol, USP was substituted, if necessary, due to alcohol permit and availability considerations.
[5]Hydroxypropyl cellulose, NF was optionally substituted in place of Hydroxypropyl Methylcellulose, USP.

Quantitative composition of the Drug

Pilocarpine hydrochloride controlled release 15 mg, 20 mg and 25 mg tablets were manufactured as detailed below from the master granulation.

Pilocarpine Hydrochloride Controlled Release 15 mg Tablets

Target Tablet Weight: 324.00 mg[1]

Tablet Toolings: ⅜" round flat face—beveled edge or equivalent

Pilocarpine Hydrochloride Controlled Release 20 mg Tablets

Target Tablet Weight: 432.00 mg[1]

Tablet Toolings: 7/16" round flat face—beveled edge or equivalent

Pilocarpine Hydrochloride Controlled Release 25 mg Tablets

Target Tablet Weight: 540.00 mg[1]

Tablet Toolings: 7/16" round flat face—beveled edge or equivalent (1) Target tablet weight may be varied ±5% on the basis of pilocarpine hydrochloride content of master granulation to obtain the target drug potency.

Quantitative Composition of the Drug

The composition of pilocarpine hydrochloride controlled release 15 mg tablets as described below were made and used for purposes of Example 2 in Phase I clinical studies.

| INGREDIENTS | LABEL CLAIM PER TABLET | QUANTITY PER TABLETS | % WW COMPOSITION |
|---|---|---|---|
| Pilocarpine hydrochloride, USP | 15.00 mg | 15.00 mg[1] | 5.0 |
| Carbomer 934P, NF | | 15.00 mg[2] | 5.0 |
| Hydroxypropyl Cellulose, NF[5] | | 30.00 mg[2] | 10.0 |
| Calcium Polycarbophil, USP | | 237.00 mg[2] | 79.0 |
| Magnesium Stearate NF | | 3.00 mg[2] | 1.0 |
| Alcohol, USP (30% v/v solution in Purified Water USP)[4] | | Qs[3] | Qs |
| Target Tablet Weight | | 300 mg | 100.0% |

[1] An overage up to 5% of label claim was usedf, if necessary to compensate for manufacturing losses.
[2] Quantity of inactive agents was adjusted from 90-110% of the indicated values.
[3] Alcohol content of granulation fluid was varied from 0 to 30% V/V depending upon the granulation and drying equipment used. The granulation fluid was removed during the drying of the granulation mass.
[4] Dehydrated Alcohol, USP was substituted, if necessary due to alcohol permit and availability considerations.
[5] Hydroxypropyl Methylcellulose, USP was optionally substituted in place of Hydroxypropyl Cellulose, NF.1

EXAMPLE 2

A U.S. FDA Phase 1 Clinical Study was conducted, in accordance with the following procedure.

Eight healthy volunteers were enrolled in the study. Each volunteer took one tablet of Pilocarpine Hydrochloride Controlled Release 15 mg Tablet every twelve hours for a total of three doses. The subjects were closely monitored during the entire study as in-patients.

The purpose of this initial clinical study was to demonstrate the safety and efficacy of a controlled-release preparation of the sialagogue pilocarpine HCl in eight healthy individuals. The specific objectives were to evaluate multiple dose tolerance, initial efficacy and initial pharmacokinetics. The eight subjects enrolled in this study were in excellent general health and were not taking any medications other than oral contraceptives. They had no complaints of oral dryness. They demonstrated normal salivary function. These volunteers spent 3 nights as inpatients at Carolinas Medical Center with two days of frequent monitoring and saliva collection. A heparinized catheter was placed in a peripheral vein in order to draw repeated blood samples. Subjects took the study drug by mouth with water at 12 hour intervals for 3 doses. Approximately 22 (10 ml) blood specimens (total 220 ml) were obtained over the course of two days. Parotid and unstimulated whole saliva were collected repeatedly using a noninvasive Carlson/Crittenden cup and a direct collection method. Patients were monitored closely for possible adverse effects.

In order to carefully monitor the eight subjects several laboratory and clinical parameters were measured. Initially, all participants underwent a complete physical exam including an EKG, urinalysis, complete blood count, electrolyte measurement, HIV testing, and liver function tests. During the three day hospital admission, the physical exam was repeated daily and the lab tests including an EKG, complete blood count, urinalysis, and electrolytes were repeated on the days which the participant took the study drug. Blood pressure, pulse and temperature were taken frequently during the hospitalization.

No toxicity or adverse effects were observed by the clinician or experienced by any subject. The dose was well tolerated and side effects such as sweating, flushing, stomach cramps, etc. commonly associated with quick release dosage forms of pilocarpine hydrochloride were not experienced by any subject.

Figure 1:
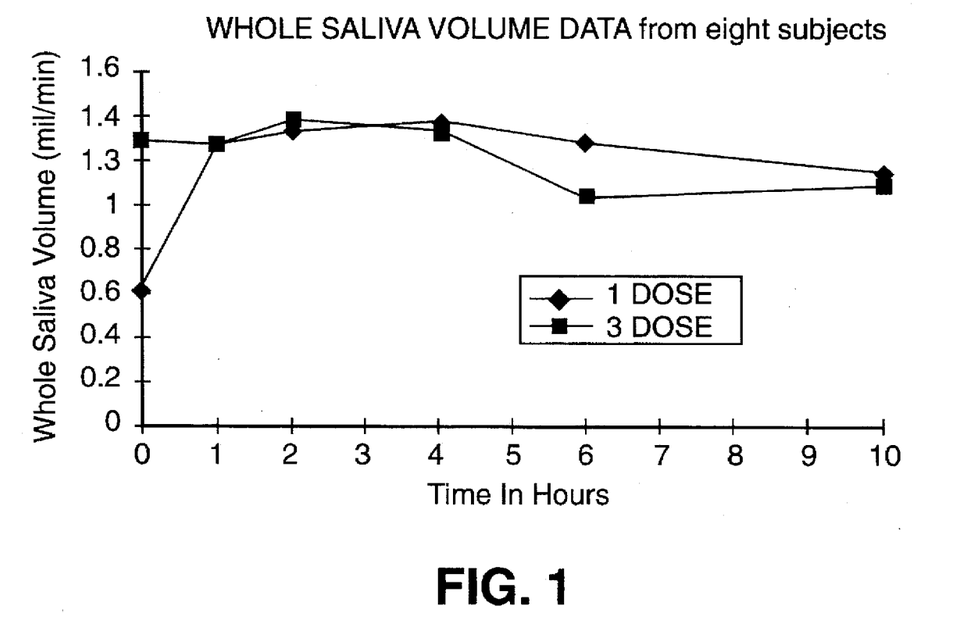
FIG. 1 depicts average whole saliva volume data (of eight subjects) measured at several different time periods during the first dose and the third dose of a composition of the present invention.
Figure 2:
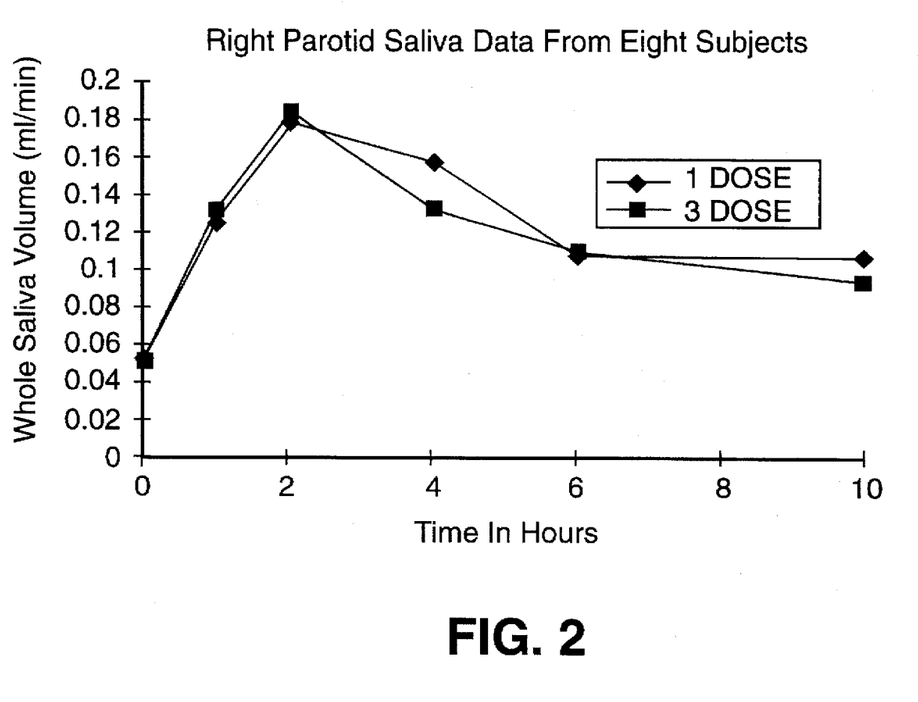
FIGS. 2 and 3, respectively, depict average (of eight subjects) right and left parotid saliva volumes after the first and third dose of a composition of the present invention.
Figure 3:
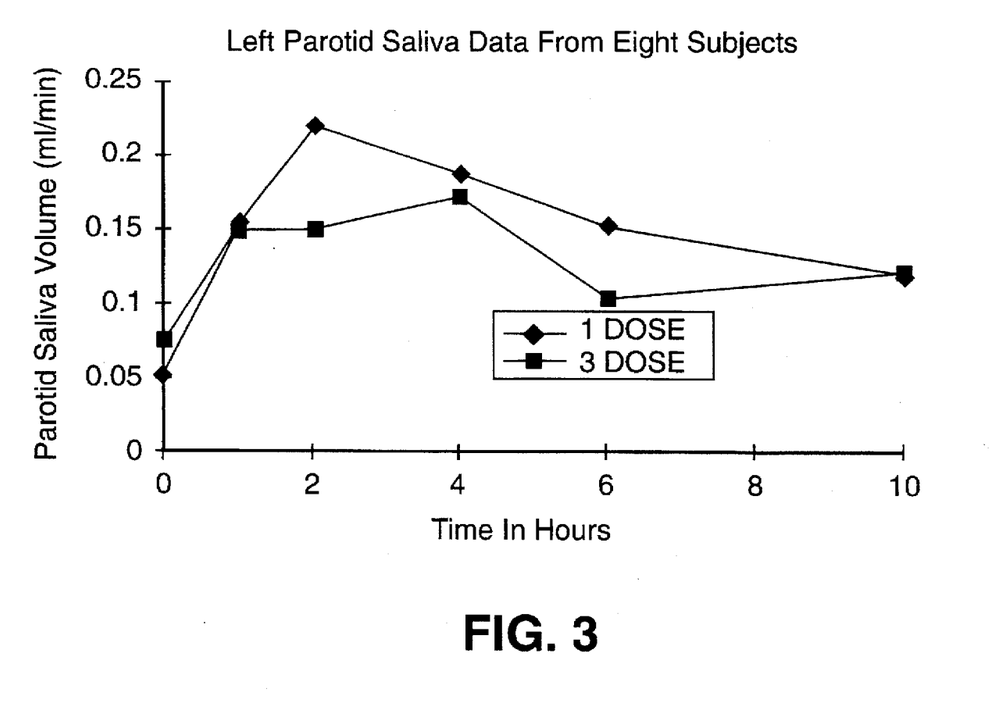

The subjects were monitored for unstimulated whole salivary flow and parotid salivary secretion after the first and third doses. The saliva volume data obtained on the eight subjects is presented in Tables 1 through 6. FIG. 1 depicts average whole saliva volume data (of eight subjects) measured at several different time periods during the first dose and the third dose. FIGS. 2 and 3, respectively, depict average (of eight subjects) right and left parotid saliva volumes after the first and third dose. The data indicate stimulation of salivary flow rates within one hour of dosing and the effects appear to last for at least about 8 to 12 hours.

Figure 4:
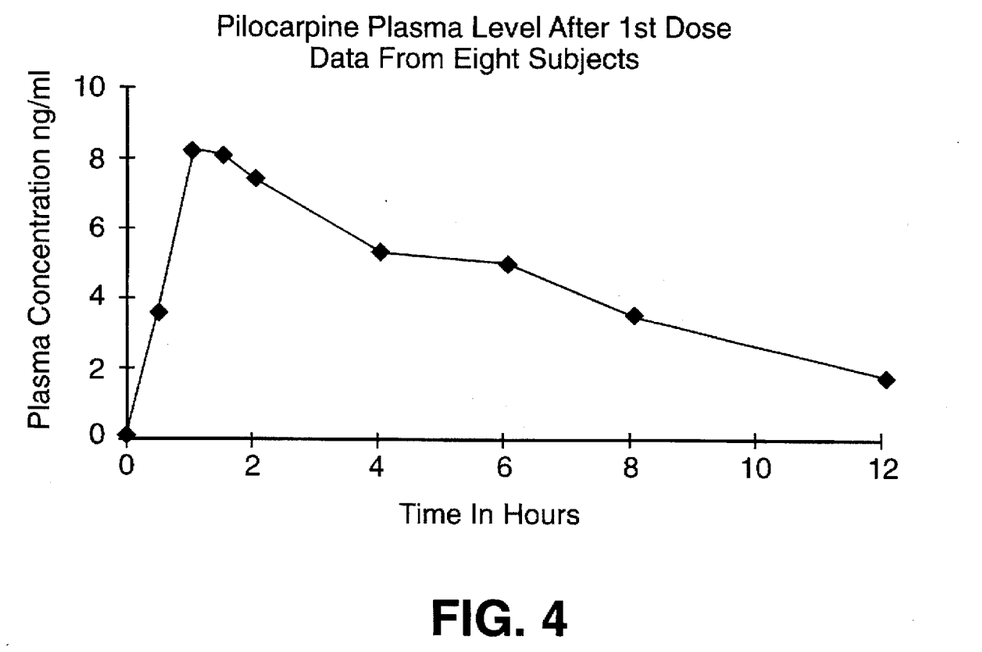
FIGS. 4 and 5, respectively, show the average plasma concentration data obtained on eight subjects, as a function of time, after the first and the third dose of a composition of the present invention.
Figure 5:
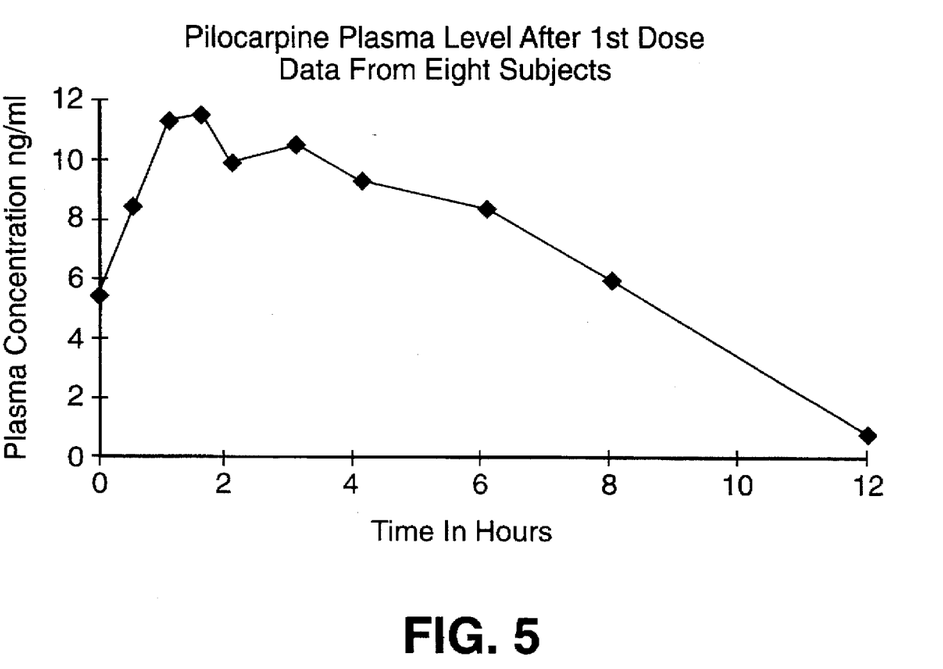

The blood samples were collected after the first and third dosing. Pilocarpine plasma concentration data obtained on the eight subjects are detailed in Tables 2 through 8. The average plasma concentration data obtained on the eight subjects as a function of time after the first and the third dose are presented in FIGS. 4 and 5, respectively. The data appears to indicate $C_{max}$ of about 8 to 12 ng/ml of pilocarpine hydrochloride. The time to reach $C_{max}$ is about one hour.

No toxicity or any adverse reactions were observed during the study. The pilocarpine hydrochloride controlled release delivery system appears to be well tolerated and side effects commonly experienced with quick release formulations of pilocarpine hydrochloride are not observed.

In all eight participants, no change was noted in the physical exams during the study. Likewise, the laboratory parameters remained stable and within normal limits throughout the study. None of the participants voiced any symptoms or complaints to suggest that they experienced any undesirable side effects of the pilocarpine. For example, none of the eight subjects noted increased sweating, flushing or gastrointestinal discomfort.

In conclusion, all participants remained healthy during the study without any evidence of adverse effects from the study drug when following the above parameters.

TABLE 1

WHOLE SALIVA VOLUME (ml/min) DATA AFTER FIRST DOSE

| Time (hrs) | #1 | #2 | #3 | #4 | #5 | #6 | #7 | #8 | Average (SD) |
|---|---|---|---|---|---|---|---|---|---|
| 0 | 0.4220 | 1.5485 | 0.9337 | 0.7097 | 0.3643 | 0.0920 | 0.5163 | 0.3162 | 0.6128 (0.4558) |
| 1 | 1.4874 | 2.7156 | 1.8097 | 1.1813 | 0.8754 | 0.5370 | 1.0507 | 0.3917 | 1.2561 (0.7509) |
| 2 | 1.7385 | 2.4964 | 1.3084 | 1.2877 | 1.4422 | 0.7005 | 1.2511 | 0.3241 | 1.3186 (0.6497) |
| 4 | 1.9149 | 2.1730 | 1.6887 | 1.3515 | 0.7060 | 0.4457 | 2.2304 | 0.4637 | 1.3710 (0.7459) |
| 6 | 1.7965 | 2.0735 | 0.8580 | 1.6622 | 0.9056 | 0.8548 | 1.4571 | 0.5658 | 1.2717 (0.5450) |
| 10 | 1.5691 | 1.5463 | 1.4390 | 1.5669 | 0.8787 | 0.4841 | 1.1737 | 0.4542 | 1.1386 (0.4760) |

TABLE 2

WHOLE SALIVA VOLUME (ml/min) DATA AFTER THIRD DOSE

| Time (hrs) | #1 | #2 | #3 | #4 | #5 | #6 | #7 | #8 | Average (SD) |
|---|---|---|---|---|---|---|---|---|---|
| 0 | 1.2436 | 3.2657 | 1.9734 | 1.4100 | 0.5895 | 0.1376 | 0.3474 | 0.2848 | 1.2815 (1.0155) |
| 1 | 1.2819 | 2.1940 | 1.7587 | 1.6108 | 0.6832 | 0.4597 | 1.4614 | 0.6177 | 1.2588 (0.6178) |
| 2 | 2.3267 | 2.5069 | 0.9502 | 1.5939 | 1.0992 | 0.3328 | 1.6792 | 0.5001 | 1.3736 (0.7960) |
| 4 | 2.2045 | 2.4601 | 1.0759 | 1.5333 | 0.6503 | 0.4797 | 1.5798 | 0.5725 | 1.3195 (0.753) |
| 6 | 1.3048 | 1.9370 | 0.4379 | 1.1032 | 0.6858 | 0.4762 | 1.8464 | 0.4662 | 1.032 (0.6168) |
| 10 | 1.5474 | 1.6840 | 0.7725 | 1.9721 | 0.5871 | 0.4492 | 1.2846 | 0.3322 | 1.078 (0.622) |
| 24 | 1.1234 | 2.0874 | 1.0340 | 1.1978 | 0.5463 | 0.0705 | 0.1794 | 0.5229 | 0.8452 (0.6565) |

TABLE 3

RIGHT PAROTID SALIVA VOLUME (ml/min) DATA AFTER FIRST DOSE

| Time (hrs) | #1 | #2 | #3 | #4 | #5 | #6 | #7 | #8 | Average (SD) |
|---|---|---|---|---|---|---|---|---|---|
| 0 | 0.0634 | N/A | 0.1172 | 0.0210 | 0.0004 | 0.0071 | 0.1142 | 0.0314 | 0.0506 (0.048) |
| 1 | 1.1662 | N/A | 0.1901 | 0.1676 | 0.0801 | 0.0342 | 0.2338 | 0.0002 | 0.1246 (0.087) |
| 2 | 0.2507 | 0.3634 | 0.2674 | 0.1367 | 0.1107 | 0.0791 | 0.1762 | 0.0476 | 0.1789 (0.107) |
| 4 | 0.1909 | 0.1778 | 0.1426 | 0.0858 | 0.2710 | 0.0375 | 0.3402 | 0.0225 | 0.158 (0.111) |
| 6 | 0.1806 | 0.0905 | 0.0742 | 0.0387 | 0.2513 | 0.0456 | 0.1559 | 0.0226 | 0.1070 (0.081) |
| 10 | 0.1189 | 0.1533 | 0.1891 | 0.1426 | 0.0106 | 0.0297 | 0.1568 | 0.0623 | 0.1080 (0.066) |

TABLE 4

RIGHT PAROTID SALIVA VOLUME (ml/min) DATA
AFTER FIRST DOSE
SUBJECTS

| Time (hrs) | #1 | #2 | #3 | #4 | #5 | #6 | #7 | #8 | Average (SD) |
|---|---|---|---|---|---|---|---|---|---|
| 0 | 0.0489 | 0.0490 | 0.0743 | 0.0131 | 0.0062 | 0.0239 | 0.1287 | 0.0444 | 0.4836 (0.039) |
| 1 | 0.2060 | 0.1157 | 0.2163 | 0.0787 | 0.0387 | 0.0482 | 0.2899 | 0.0584 | 0.1315 (0.094) |
| 2 | 0.2987 | 0.2005 | 0.2297 | 0.1201 | 0.3367 | 0.0422 | 0.2182 | 0.0382 | 0.1850 (0.1100) |
| 4 | 0.1258 | 0.3032 | 0.1107 | 0.0596 | 0.1054 | 0.0897 | 0.2489 | 0.0215 | 0.133 (0.095) |
| 6 | 0.1611 | 0.1517 | 0.0611 | 0.0886 | 0.0871 | 0.0413 | 0.2413 | 0.0460 | 0.110 (0.069) |
| 10 | 0.0907 | 0.1719 | 0.1716 | 0.0288 | 0.0755 | 0.0755 | 0.1069 | 0.0398 | 0.0944 (0.053) |
| 24 | 0.0591 | 0.1626 | 0.1025 | 0.0429 | 0.0429 | 0.0021 | 0.0506 | 0.0016 | 0.058 (0.053) |

TABLE 5

LEFT PAROTID SALIVA VOLUME (ml/min) DATA
AFTER FIRST DOSE
SUBJECTS

| Time (hrs) | #1 | #2 | #3 | #4 | #5 | #6 | #7 | #8 | Average (SD) |
|---|---|---|---|---|---|---|---|---|---|
| 0 | 0.0146 | N/A | 0.1295 | 0.0081 | 0.0010 | 0.0101 | 0.1916 | 0.0057 | 0.0915 (0.0767) |
| 1 | 0.1280 | 0.1251 | 0.3541 | 0.0399 | 0.0744 | 0.1532 | 0.2800 | 0.0735 | 0.1535 (0.109) |
| 2 | 0.1801 | N/A | 0.5794 | 0.0519 | 0.2957 | 0.0986 | 0.2718 | 0.0599 | 0.2190 (0.186) |
| 4 | 0.1169 | N/A | 0.2760 | 0.1118 | 0.2177 | 0.1460 | 0.3471 | 0.0781 | 0.1857 (0.098) |
| 6 | 0.0936 | 0.1200 | 0.2364 | 0.2561 | 0.1946 | 0.0660 | 0.2207 | 0.0266 | 0.1520 (0.086) |
| 10 | 0.0816 | 0.1119 | 0.3158 | 0.0682 | 0.0105 | 0.0108 | 0.2616 | 0.0797 | 0.1180 (0.112) |

TABLE 6

LEFT PAROTID SALIVA VOLUME (ml/min) DATA
AFTER THIRD DOSE
SUBJECTS

| Time (hrs) | #1 | #2 | #3 | #4 | #5 | #6 | #7 | #8 | Average (SD) |
|---|---|---|---|---|---|---|---|---|---|
| 0 | 0.0187 | 0.0810 | 0.1059 | 0.0428 | 0.0006 | 0.0873 | 0.1786 | 0.0730 | 0.0735 (0.055) |
| 1 | 0.1237 | 0.2735 | 0.2469 | 0.0582 | 0.0004 | 0.0793 | 0.03452 | 0.0056 | 0.1478 (0.1243) |
| 2 | 0.1494 | 0.1327 | 0.2743 | 0.0524 | 0.2039 | 0.0213 | 0.2709 | 0.0855 | 0.1490 (0.095) |
| 4 | 0.1174 | 0.1527 | 0.4517 | 0.1144 | 0.0917 | 0.0562 | 0.3279 | 0.0541 | 0.1710 (0.142) |
| 6 | 0.0744 | 0.0852 | 0.1131 | 0.0562 | 0.0821 | 0.0128 | 0.3552 | 0.0493 | 0.1030 (0.105) |
| 10 | 0.0709 | 0.1411 | 0.2128 | 0.1547 | 0.0623 | 0.0314 | 0.2432 | 0.0430 | 0.1200 (0.080) |
| 24 | 0.0181 | 0.1523 | 0.0854 | 0.0483 | 0.0491 | 0.0031 | 0.0764 | 0.0172 | 0.0560 (0.048) |

TABLE 7

PILOCARPINE PLASMA LEVEL (ng/ml) DATA AFTER FIRST DOSE SUBJECTS

| Time (hrs) | #1 | #2 | #3 | #4 | #5 | #6 | #7 | #8 | Average (SD) |
|---|---|---|---|---|---|---|---|---|---|
| 0 | 0 | 0 | 0 | 0 | 0 | 0 | 0 | 0 | 0 |
| 0.5 | 5.4 | 0 | 0 | 0 | 0 | 7.0 | 15.6 | 0 | 3.5 (5.7) |
| 1.0 | 11.1 | 11.6 | 6.8 | 8.1 | 5.9 | 7.9 | 9.0 | 5.5 | 8.2 (2.2) |
| 1.5 | 10.5 | 8.2 | 9.6 | 6.3 | 5.9 | 10.0 | 8.5 | 5.7 | 8.1 (1.9) |
| 2 | 10.3 | 11.5 | 11.7 | 0 | 7.2 | 7.3 | 5.8 | 5.7 | 7.4 (3.8) |
| 4 | 6.9 | 6.9 | 6.4 | 0 | 8.5 | 6.7 | 8.5 | 0 | 5.3 (3.4) |
| 6 | 7.0 | 5.6 | 5.2 | 0 | 5.4 | 8.4 | 8.7 | 0 | 5.0 (3.4) |
| 8 | 9.1 | 6.3 | 6.3 | 0 | 6.0 | 0 | 0 | 0 | 3.5 (3.8) |
| 12 | 0 | 0 | 0 | 0 | 5.3 | 0 | 8.9 | 0 | 1.8 (3.4) |

TABLE 8

PILOCARPINE PLASMA LEVEL (ng/ml) DATA AFTER THIRD DOSE SUBJECTS

| Time (hrs) | #1 | #2 | #3 | #4 | #5 | #6 | #7 | #8 | Average (SD) |
|---|---|---|---|---|---|---|---|---|---|
| 0 | 5.7 | 14.8 | 10.3 | 0 | 0 | 0 | 6.9 | 5.1 | 5.4 (5.4) |
| 0.5 | 12.0 | 8.8 | 12.1 | 6.0 | 7.0 | 8.9 | 12.0 | 0 | 8.4 (4.1) |
| 1.0 | 10.1 | 11.5 | 12.9 | 7.9 | 11.3 | 6.5 | 18.1 | 11.8 | 11.3 (3.5) |
| 1.5 | 9.0 | 11.7 | 7.7 | 10.8 | 14.6 | 8.0 | 24.3 | 6.1 | 11.5(5.8) |
| 2.0 | 12.6 | 11.6 | 10.8 | 8.2 | 6.9 | 8.9 | 14.6 | 5.9 | 9.9(3.0) |
| 3.0 | n/a | 14.1 | 9.1 | 7.1 | 11.0 | 11.5 | 15.5 | 5.5 | 10.5(3.6) |
| 4.0 | 8.5 | 11.9 | 9.9 | 6.5 | 10.0 | 12.6 | 8.5 | 6.4 | 9.3(2.3) |
| 6.0 | 6.3 | 10.5 | 5.2 | 6.1 | 7.7 | 9.5 | 11.7 | 9.8 | 8.4(2.4) |
| 8.0 | 9.7 | 7.6 | 0 | 6.3 | 5.7 | 12.3 | 6.5 | 0 | 6.0(4.3) |
| 12.0 | 0 | 6.7 | 0 | 0 | 0 | 0 | 0 | 0 | 0.8(2.4) |

What is claimed is:

1. A method for treating a patient suffering from xerostomia, comprising orally administering to said patient an extended release formulation comprising a therapeutically effective amount of pilocarpine, or a pharmaceutically acceptable salt thereof and a pharmaceutically acceptable extended release carries in an amount sufficient to maintain a blood serum level of pilocarpine in said patient of from about 5 to about 40 ng/ml, for a period of at least 6 hours.

2. The method of claim 1 wherein the patient is to receive radiotherapy and the pilocarpine is administered prior to the commencement of radiotherapy.

3. The method of claim 1 wherein the patient is to receive chemotherapy and the pilocarpine is administered prior to the commencement of chemotherapy.

4. The method of claim 1 wherein the xerostomia is chemically induced xerostomia.

5. The method of claim 1 wherein the xerostomia is age related xerostomia.

6. The method of claim 1 wherein the xerostomia is seasonal induced xerostomia.

7. The method of claim 1, wherein the therapeutically effective amount of pilocarpine or a pharmaceutical acceptable salt thereof is orally administered in a unit dosage form comprising an intimate admixture of pilocarpine and calcium polycarbophil, wherein from about 5 to abut 30 mg of pilocarpine is present and the ratio of calcium polycarbophil to pilocarpine is from about 10:1 to about 20:1.

8. A formulation in unit dosage form comprising an intimate admixture of pilocarpine and calcium polycarbophil, wherein from about 5 to about 30 mg of pilocarpine is present and the ratio of calcium polycarbophil to pilocarpine is from about 10:1 to about 20:1.

* * * * *